US008868201B2

(12) United States Patent
Roberts et al.

(10) Patent No.: US 8,868,201 B2
(45) Date of Patent: Oct. 21, 2014

(54) ADAPTIVELY CONFIGURING THE VALIDATION TIMEOUT OF A SESSION KEY USED FOR SECURING COMMUNICATION WITH AN IMPLANTABLE MEDICAL DEVICE

(75) Inventors: Earle T. Roberts, Maple Grove, MN (US); Irfan Z. Ali, Woodbury, MN (US); Donald L. Villalta, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 26 days.

(21) Appl. No.: 13/446,074

(22) Filed: Apr. 13, 2012

(65) Prior Publication Data

US 2012/0271380 A1 Oct. 25, 2012

Related U.S. Application Data

(60) Provisional application No. 61/477,331, filed on Apr. 20, 2011.

(51) Int. Cl.
*A61N 1/37* (2006.01)
*H04L 9/08* (2006.01)
*H04W 12/04* (2009.01)
*A61N 1/372* (2006.01)
*H04L 29/06* (2006.01)

(52) U.S. Cl.
CPC ............ *H04W 12/04* (2013.01); *H04L 9/0891* (2013.01); *A61N 1/37258* (2013.01); *H04L 63/0435* (2013.01); *H04L 2209/805* (2013.01); *H04L 2209/88* (2013.01); *H04L 63/068* (2013.01); *H04L 9/088* (2013.01); *A61N 1/37252* (2013.01)
USPC ............................................... 607/60; 607/61

(58) Field of Classification Search
USPC ....................................................... 607/60, 61
See application file for complete search history.

(56) References Cited

U.S. PATENT DOCUMENTS

| 7,475,245 | B1 | 1/2009 | Healy et al. |
| 7,565,197 | B2 | 7/2009 | Haubrich et al. |
| 7,930,543 | B2 | 4/2011 | Corndorf |
| 8,102,999 | B2 | 1/2012 | Corndorf |
| 2007/0224978 | A1 | 9/2007 | Wherry et al. |
| 2007/0282398 | A1 | 12/2007 | Healy et al. |
| 2009/0144546 | A1 | 6/2009 | Jancula et al. |
| 2009/0292340 | A1 | 11/2009 | Mass et al. |
| 2011/0066211 | A1 | 3/2011 | Von Arx et al. |

OTHER PUBLICATIONS

International Search Report and Written Opinion, dated Sep. 10, 2012, PCT/US2012/033428, 12 pages.

*Primary Examiner* — Joseph Dietrich
(74) *Attorney, Agent, or Firm* — Withers & Keys, LLC

(57) ABSTRACT

Methods, devices and systems are disclosed that provide for dynamically adjusting the valid lifespan of a session key for wireless communication sessions established between at least two medical devices. Adjusting the session key lifetime balances protecting the communications link so that it is not unnecessarily susceptible to eavesdropping by third parties or other interference while obviating the need for a user to repeatedly perform access control steps.

25 Claims, 9 Drawing Sheets

ADAPTIVELY CONFIGURING THE VALIDATION TIMEOUT OF A SESSION KEY USED FOR SECURING COMMUNICATION WITH AN IMPLANTABLE MEDICAL DEVICE

PRIORITY

This application claims the benefit of U.S. Provisional Application No. 61/477,331, filed Apr. 20, 2011, the entire contents of which are incorporated herein by reference.

FIELD

The present disclosure relates generally to providing secure communications in a data communications setting, particularly in providing security in telemetry between an implantable medical device and other implantable or external devices.

BACKGROUND

A variety of implantable medical devices (IMDs) exist that provide diagnostic or therapeutic capabilities. These IMDs include, for example, tissue, organ and nerve stimulators and/or sensors, cardiac pacemakers, and implantable cardioverters/defibrillators. It has become common to provide a communication link between an IMD and an external programmer or other external medical device (EMD) in order to provide for communication of commands and to allow for transmission of stored information and/or sensed physiological parameters between the IMD and the EMD.

Wireless telecommunications are ideally suited for IMDs and to date are the best way to regularly exchange information with the IMD while it remains in its implanted state. Accordingly, the use of telecommunications for IMD administration may include communications to or from an IMD, and may concern wireless transmission of collected measurements and/or instructions.

SUMMARY

In general, the disclosure relates to methods and systems for providing secure communications in a data communications setting.

Various embodiments concern a method for adjusting a timeout period of a communication session, comprising establishing a communication session between an implantable medical device and at least one other device, wherein a session key is transmitted between the implantable medical device and the at least one other device in establishing the communication session, the session key allowing one or both of programming of the implantable medical device by the at least one other device and decryption of information transmitted between the implantable medical device and the at least one other device during the communication session. Such methods can further include setting a time period interval of the session key, receiving a communication session close trigger event, performing a count of the time period interval based on the reception of the communication session close trigger event, and disabling the session key in response to expiration of the time period count, wherein each of establishing, setting, receiving, performing, and disabling are each performed at least in part by the implanted medical device and the at least one other device. In some embodiments, the time period count is performed by the device of the plurality of devices to which the session key was transmitted. Also, the method may include generating an alert to a user based on the count of the time period interval.

Such embodiments may include that the time period interval is set before the session key is transmitted between the implantable medical device and the at least one other device in establishing the communication session.

Such embodiments may further include evaluating a time duration for each of a plurality of previous communication sessions involving the implantable medical device and the at least one other device, wherein the time period interval of the session key is set based on the evaluation of the time duration for each of the plurality of previous communication sessions. Setting the duration of the time period may comprises evaluating at least one predefined criteria to determine the time period. Predefined criteria may include a category of a clinical procedure indicated to be performed as part of the communication session. In some embodiments, establishing the communication session comprises generating the session key, wherein the session key is generated by the at least one other device and is ephemeral.

Various method embodiments further include receiving an indication of activity during the time period count, and resetting the time period count responsive to receiving the indication of activity. The trigger events may include an inactivity interval, a session link loss indication, a close service request, expiration of a predefined interval, and a communication session interruption.

Various embodiments concern a system for adjusting a timeout period of a communication session in transcutaneous communications. Such a system my comprise an implantable medical device having communication circuitry and an external device having communication circuitry, the communication circuitry of the implantable medical device and the communication circuitry of the external device configured to establish a communication session between the implanted medical device and the external device and to transmit a session key between the communication circuitry of the implantable medical device and the communication circuitry of the external device in establishing the communication session, the session key allowing decryption of information transmitted between the implanted medical device and the external device. Such system embodiments may further include control circuitry comprising a processor and memory storing program instructions executable by the processor, the control circuitry configured to set a time period interval of the session key, receive a communication session close trigger event, perform a count of the time period interval based on the reception of the communication session close trigger event, and disable the session key in response to expiration of the time period count. Control circuitry may further be configured to evaluate a time duration for each of a plurality of previous communication sessions involving the implanted medical device and the external device, wherein the time period interval of the session key is set based on the evaluation of the time duration for each of the plurality of previous communication sessions. The control circuitry may be distributed between the implantable medical device and the external device.

Control circuitry may be configured to perform one or more of evaluate at least one criterion and set the duration of the time period based on the evaluation of the at least one criterion, generate the session key as part of establishing the communication session and the session key is ephemeral, disable the session key by invalidating the session key for allowing decryption of information transmitted between the implanted medical device and the external device, receive an indication of communication activity during the time period count and reset the time period count responsive to receiving the indication of communication activity, generate an alert to a user based on the count of the time period interval, and receive an indication that establishment of the communication session is desired by a user, wherein the evaluation of the at least one criteria determines a category of a clinical procedure and the control circuitry sets the duration of the time period based on the category for the communication session.

Various embodiments concern a system for adjusting a timeout period of a communication session comprising means for establishing a communication session between an implanted medical device and at least one other device, wherein a session key is transmitted between the implanted medical device and the at least one other device in establishing the communication session, the session key allowing one or both of programming of the implanted medical device by the at least one other device and decryption of information transmitted between the implanted medical device and the at least one other device during the communication session. System embodiments may further include means for setting a time period interval of the session key, means for receiving a communication session close trigger event, means for performing a count of the time period interval based on the reception of the communication session close trigger event, and means fir disabling the session key in response to expiration of the time period count. Such system embodiments may further include any of the aspects referenced herein.

Various embodiments concern a computer readable medium comprising instructions for causing a medical device to adjust a timeout period of a communication session comprising establishing a communication session between an implanted medical device and at least one other device, wherein a session key is transmitted between the implanted medical device and the at least one other device in establishing the communication session, the session key allowing one or both of programming of the implanted medical device by the at least one other device and decryption of information transmitted between the implanted medical device and the at least one other device during the communication session. Instructions may also be executable for setting a time period interval of the session key, receiving a communication session close trigger event, performing a count of the time period interval based on the reception of the communication session close trigger event, and disabling the session key in response to expiration of the time period count. Such embodiments can utilize any of the features or options listed above or otherwise referenced herein.

Various embodiments concern a method for adjusting a timeout period of a. transcutaneous communication session with an implantable medical device, comprising: establishing a transcutaneous communication session, wherein a session key is transmitted transcutaneously in establishing the communication session, the session key allowing one or both of programming of an implantable medical device and decryption of information transmitted transcutaneously during the communication session; setting a time period interval of the session key; receiving a communication session close trigger event; performing a count of the time period interval based on the reception of the communication session close trigger event; and disabling the session key in response to expiration of the time period count, wherein each of establishing, setting, receiving, performing, and disabling are each performed at least in part by control circuitry of the implantable medical device.

Various embodiments concern an implantable medical device, comprising: communication circuitry configured to establish a communication session between the implanted medical device and an external device and to receive a session key from the external device in establishing the communication session, the session key allowing decryption of information transmitted between the implanted medical device and the external device, the session key having a time period interval that is dynamically set by either of the external device and the implantable device; and control circuitry configured to receive a communication session close trigger event, perform a count of the time period interval based on the reception of the communication session close trigger event, and disable the session key in response to expiration of the time period count.

The details of one or more examples are set forth in the accompanying drawings and the description below. Other features, objects, and advantages will be apparent from the description and drawings, and from the claims.

DETAILED DESCRIPTION OF THE ILLUSTRATED EMBODIMENTS

Figure 1:
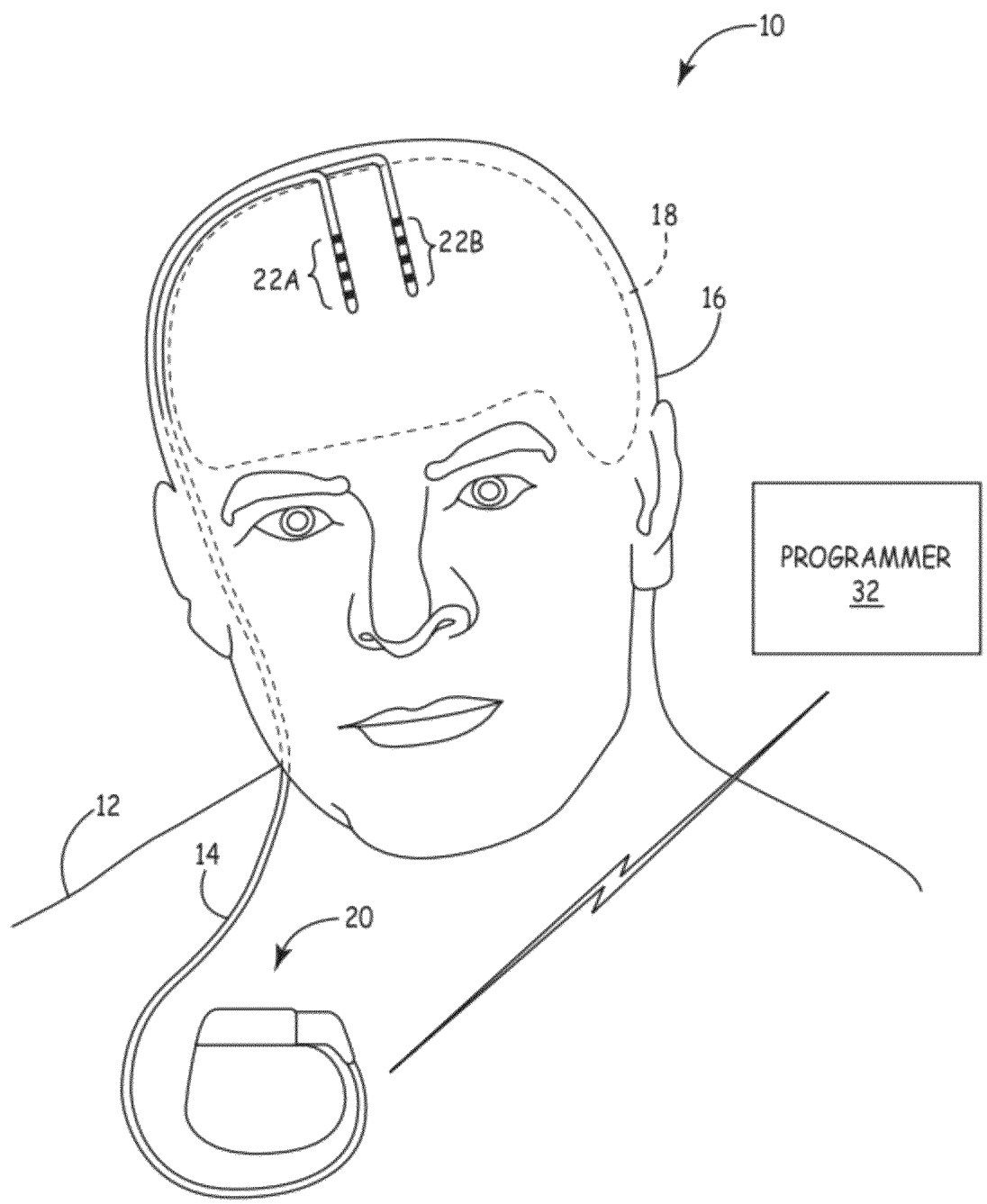
FIG. 1 is a conceptual diagram illustrating a device network.

Various techniques are disclosed herein for dynamically adjusting the valid lifespan of a session key established for a secure communication session between a plurality of devices, such as an IMD and an external medical device (EMD). The techniques may involve the evaluation of one or more inputs to determine a time interval for the duration of a validation lifetime for a session key.

Various medical information privacy laws, including the Health insurance Portability and Accountability Act (HIPAA) and the European Privacy Directive underscore the importance of safeguarding patient privacy and require the protection of all patient-identifiable health information (PHI). Under HIPAA, PHI is defined as individually identifiable patient health information, including identifiable demographic and other information relating to the past, present or future physical or mental health or condition, or the provision or payment of health care to an individual that is created or received by a health care provider, health plan, employer or health care clearinghouse. Other types of sensitive information in addition to or in lieu of PHI could also be protectable.

The advent of wireless communication into the realm of implantable medical devices has therefore come with the need for stricter communication security methods to safeguard data, among other things. This is due, in part, to the fact that some of the wireless communication protocols that may be suitable to IMD telemetry applications are of a "broadcast" nature, rather than of a directionally limited nature. Accordingly, if a device having wireless communications capability is in range of a telemetry signal (such as a signal containing data originating from an IMD or an instructional signal intended for an IMD) the device may receive the signal, regardless of whether the receiving device was the target. Likewise, the IMD may also be in range of transmitting devices that may transmit signals to the IMD inadvertently, such as in the case of multiple programming sessions occurring in the same clinic.

Establishing a communication session between an IMD and an EMD may be an energy consuming process that may take up valuable resources of the IMD, such as power. The process may also be time consuming for clinical professionals and may be especially inconvenient in sterile fields typically encountered during implantation procedures. In some cases, a communication session may require the communicating devices to at least initially be within a very limited range for inductive communication to take place before longer range wireless communication can be used to continue the session. For example, the antennas of a programmer and an IMD may need to be within a few inches of each other to form an inductive communication link between the two devices, initially requiring an inductive link serves as a security measure as the patient and/or clinician can limit unwelcome persons form getting close enough (e.g., an antenna of the external device within an inch or two of the external device) to create the inductive link. Once the inductive link is formed, a code and/or session key can be passed between the devices, such as the external device sending the code and/or session key to the IMD. If a code is sent to the IMD uniquely identifying the programmer, a session key may be sent having the code to verify that the same devices continue to communicate. The session key may later facilitate secure radio frequency communication (e.g., using Bluetooth) between the same device, which can permit a much longer distance between the devices (e.g., up to 30 feet in some implementations). The longer distance may be desirable for some programming sessions, such as when a patient must move about the room when trying out therapy parameters, go to another room to use other testing equipment, or go to a bathroom, for example.

It is therefore desirable to minimize the frequency of initiation of communication sessions. For example, in the above scenario of initializing a communication session with an inductive link, reinitializing the communication session may require that the programmer enter the sterile field of an operating environment to again position the programmer antenna within a very close range of the IMD to form an inductive link. The limiting of the frequency of communication session initiation can further be balanced with limiting the time duration during which an IMD may be susceptible to, for example, repeated attempts by malicious users to retry communication attempts using different key values, should a patient leave a medical environment without formally terminating the communications session or a communication session otherwise remain open for an unduly long period.

The present disclosure provides systems and methods for adaptively adjusting the valid lifespan of a session key that is used for communication between two or more medical devices. In various embodiments, the session key may be an ephemeral key having a time limit that varies from one communication session to the next session. The time limit can be set for each communication session and can be set based on the expected nature of an impending communications session or a characteristic of previous communication sessions.

The dynamic nature of the ephemeral key can reduce the incidence of premature termination of a communication session and the need fir repeated authentication steps, whereby premature termination of a session key may otherwise result in termination of the communication session and necessitate re-connection and initiation of a new communication session between previously connected devices. The ephemeral nature of the session key limits the reuse of the session key inadvertently and reduces susceptibility of live communication channels in a network of communicating devices.

In various embodiments, a heuristic technique for adjusting the validation lifetime of a session key is disclosed. The heuristic method can be based on user inputs, user activity patterns, the nature of the programming activity flow, link quality, the time between the initiation of a connection request and the grant of the request, and/or user or selectable security settings such as perceived interruptions or eavesdropping. By using these inputs appropriately, the technique calculates a predetermined or heuristically determined time interval for the invalidation of a session key.

In various embodiments, a device includes an algorithm that determines the amount of time that a session key remains valid under certain conditions (e.g., periods of user inactivity) to limit the life of the key while also avoiding invalidating the key prematurely. The session key may be maintained on a secure repository or generated by a device, such as on a programmer, and is transmitted to another device, such an BID, for communication until the session key's validity times out. As such, in various embodiments, the key may be generated by an EMD and/or stored on the EMD and shared with a communicating partner (e.g., IMD), provided that any necessary access control mechanisms have been met to establish a secure communication session between the communicating devices. In various embodiments, the IMD is responsible for monitoring for key expiry because the IMD has particular vulnerabilities to unauthorized communications (e.g., an inadvertent or malicious programming command). In which case, the IMD can delete the session key upon expiration and not recognize programming commands or transmit patient information until a new communication session has been established and another session key is received.

Various embodiments include establishing a count of a predetermined time interval when one or more predefined conditions are met. The count may be a count-down or a count-up of the predetermined time interval. Upon the lapse of the predetermined time interval, the validation lifetime of the session key utilized by the IMD and the EMD is terminated, thereby terminating the secure communication session between the IMD and the EMD. Subsequent communications would require that the access control steps be reissued.

Various embodiments of the present disclosure concern techniques for dynamically adjusting the valid lifespan of a session key established for a secure communication session between a plurality of devices, such as an MID and an EMD. The techniques may involve the evaluation of one or more inputs to determine a time interval for the duration of a valid lifetime for a session key. In other words, a predetermined duration is provided that defines when a session key will be invalidated, or the process by which the session key will be invalidated, thereby terminating the communication session.

In various embodiments, the valid lifespan of a session key may be determined autonomously by the IMD through evaluation of one or more associated inputs, or a specific duration may be provided by the EMD or by a user. The IMD or programmer may "learn" the appropriate inputs for the evaluation of a validation lifespan and a predetermined duration is set based on the evaluation. In particular, a device may associate various parameter values with the session key lifetime, and then automatically determine the lifespan duration according to these parameters. It should be noted however, that the illustrative determination by the IMD of the valid lifespan described is merely exemplary and it is contemplated that the EMD, or another device associated with either the IMD or EMD, may also perform this function in various embodiments.

For example, the IMD may store a table or other data structure that contains records, in which each record contains information associated with a respective value of session key lifespan duration. The IMD may automatically update the table in response to adjustments from the user, or may update the table after receiving user overrides to adjust the lifespan of the session key. The IMD may update the program table after every adjustment input from the user, or after multiple override requests. The table may also be adjusted based on a history of communication sessions, such as a parameter of average communication session length.

In various embodiments, an IMD my autonomously determine the timeout duration or other aspects of a session key based on the lifecycle of the IMD. For example, the manufacturing data (e.g., plant), shelf life, sterilization procedure, history, battery information, or other information related to the history of the IMD may be used to generate a session key.

FIG. 1 is a conceptual diagram illustrating an exemplary device network in conjunction with a patient. As shown in FIG. 1, device network 10 includes an IMD 20 and lead 14 implanted within patient 12. Specifically, lead 14 enters through cranium 16 and is implanted within brain 18 to deliver deep brain stimulation (DBS). Although a DBS application of an IMD is used in this example, it will be appreciated that the techniques disclosed herein are applicable to any IMD for which a secure communication session can be established, including but not limited to cardiac stimulators, spinal cord stimulators, peripheral nerve stimulators, drug delivery devices (e.g., implantable drug pumps), and implantable monitoring devices. Electrodes 22A and 22B of lead 14 provide electrical pulses to surrounding anatomical regions of brain 18 in a therapy that may alleviate a condition of patient 12. In some embodiments, more than one lead 14 may be implanted within brain 18 of patient 12 to stimulate multiple anatomical regions of the brain. Device network 10 further includes programmer 32 that may be a handheld device, portable computer, or workstation that communicates with IMD 20. IMD 20 and programmer 32 in the device network communicate through a wireless communication link.

Figure 2:
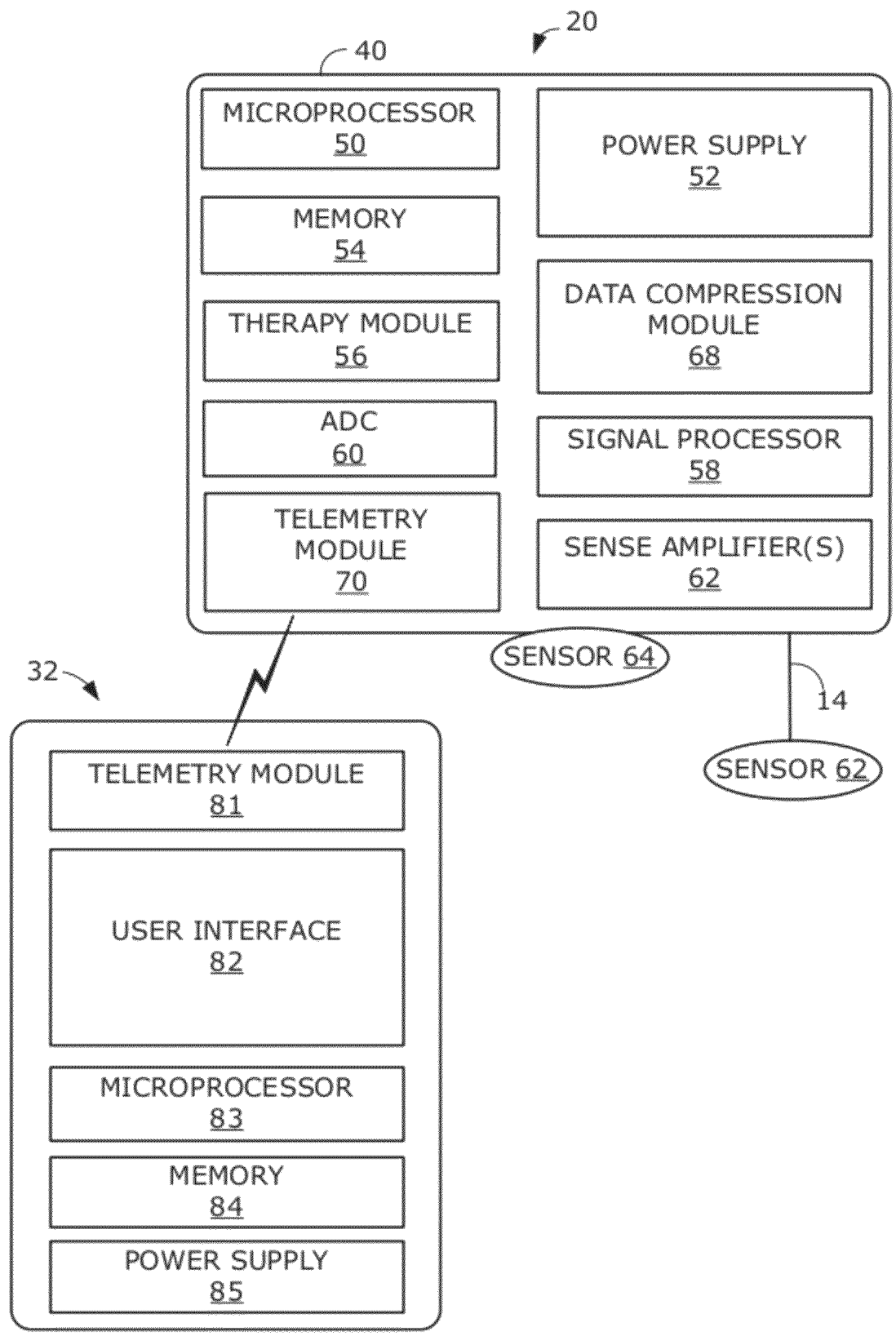
FIG. 2 is a block diagram illustrating various components of an IMD.

FIG. 2 is a block diagram illustrating some, but not necessarily all, of the components that can be included in IMD 20. IMD 20 includes an appropriate housing 40 enclosing various components, including control circuitry. Control circuitry can include one or more of an application specific integrated circuit (ASIC), an electronic circuit, one or more processors (shared, dedicated, or group) and memory that execute one or more software or firmware programs, a combinational logic circuit, or any combination of these and other suitable components that are specially configured to provide the described functionality, as will be further described herein.

A processor 50 can be provided along with a power supply 52, the latter of which usually includes a battery and a capacitor. Memory 54 is provided in various forms that include one or more units of memory that can store operating instructions and/or data collected by the IMD 20. Memory 54 can be volatile or non-volatile. IMD 20 includes a therapy module 56 that generally includes the components and instructions to provide one or more therapies, if the IMD 20 is so equipped. Examples may include neural stimulation, drug delivery, pacing, defibrillation, and so on, depending on the application. A signal processor 58 receives and processes data. An analog to digital converter (ADC) 60 receives a raw or processed analog signal and converts that signal into digital data. Processor 50 and memory 54 are examples of control circuitry for performing the various functions described herein. Processor 50 may be a microprocessor or other processing component.

IMD 20 also includes a sense amplifier 62 that receives data from one or more sensors (e.g., 62, 64) and then outputs an amplified signal to other components within IMD 20. In various embodiments, one or more sensors may be coupled directly with the housing 40 (e.g., sensor 64). In various embodiments, one or more sensors may be remotely coupled to the housing 40 (e.g., sensor 62 via a lead 14 or through wireless communication). In various embodiments, one or more sensors may be located within the housing 40. To maximize resources, IMD 20 may include a data compression module 68 that compresses data before storing that data into memory 54. When physiologic data, for example, is collected by IMD 20, it may be stored in memory 54 until it is wirelessly transmitted out, or IMD 20 is extracted, or the memory capacity is exceeded and the data is overwritten. In some cases, the physiologic date is sent through a secured wireless communication link., the wireless communication link secured by authenticating protocol.

IMD 20 further includes a telemetry module 70. In various embodiments, the telemetry module 70 includes an RF (radio frequency) transceiver (not shown), which interfaces through telemetry with a remote RF transceiver in programmer 32. The telemetry module 70 may additionally or attentively include inductance components for very short distance wireless communication based on inductance. The transceiver is integrated into the IMD 20 with an antenna that may also be coupled to IMD 20. Telemetry module per nits two-way communication between IMD 20 and a patient external device (e.g., a programmer 32) and/or another implanted device. RF communication may be performed either by varying the frequency, phase angle, amplitude, and/or other parameter of the electromagnetic energy radiated by the on-board RF transceiver. In a further embodiment, one or more repeaters (e.g., in a programmer or other device) augment the long range telemetric communication by relaying the telemetric signals from telemetry module 70 to a secure server, which can provide secure on-line data access over a network, such as the Internet, to authorized health care providers and medical professional.

Processor 50 may control the operation of the IMD 20, including operation of the transceiver, as control circuitry. The general operation of processor 50 and other control circuitry may be appreciated by reference to the exemplary algorithms of the flowcharts depicted in FIGS. 3-9. Those skilled in the art will appreciate that the flowcharts illustrated herein may be used to represent software or firmware that may be executed by control circuitry (e.g., processor 50 or other chip hardware) configured to perform the functions set forth in the flowchart or otherwise outlined herein as part of control circuitry. Hardware may also be control circuitry configured to carry about functions described herein. Memory 54 may additionally store software which may be used to control the operation of the IMD. Thus, hardware, software, firmware, or any combination of the three, may be employed without departing from the spirit and scope of the instant disclosure.

FIG. 2 further illustrates a programmer 32 configured to conduct transcutaneous communication sessions with the IMD 20. The programmer 32 is an EMD that may be used by a clinician, patient, or other user for establishing and conducting a communication session through one or more wireless protocols. The programmer 32 may be used to program the IMD 20, such as instructing the IMD 20 on how to carryout therapy delivery. The programmer 32 may also receive information from the IMD 20, such as sensed data. Wireless communication is facilitated by the telemetry module 81 of the programmer 32. The telemetry module 81 may contain circuitry for conducting wireless communication with the telemetry module 70 of the IMD 20. The telemetry module 81 may contain circuitry for near-field (e.g., inductance limited to a few inches) and/or far field (e.g., radio frequency for a body area network) communication. In some embodiments, a telemetry module may be configured to switch between near-field (e.g., transmitting only a few inches) and far-field communication (e.g., transmitting at least a few feet and substantially farther than near-field communication). In some embodiments, a secure communication session can only be initiated by near-field communication (e.g., inductance signals) but after initiation will be conducted via far-field communication (e.g., radiofrequency signals) as the communications modules switch between near-field and far-field communication. In some embodiments, a session key will only be passed between two devices establishing a secure communication session by near-field communication. Near-field transmission of a session key can minimize the chance that a third (unauthorized or otherwise unintended) device will be close enough to receive the session key. After the session key is shared between the two devices intended to have the session key, the communication circuitry of the two devices can then switch to far-field communication to conduct the remainder of the secure communication session at much farther ranges. In some embodiments, the same type of signals are used for both near-field and far-field communications, but some aspect of signal transmission is changed between near-field and far-field communication to severally limit the broadcast range of the near-field signals. For example, circuitry transmitting RF signals in a near-field mode may operate at low power such that the range of the RF signals is very short, while the circuitry transmitting RF signals in a far-field mode may operate at normal or high power such that the range of the RF signals is far greater than when the circuitry operates in the near-field mode.

The programmer 32 further includes a user interface 82 for displaying information to the user and/or allowing the user to input information, such as commands. The user interface 82 may comprise one or more buttons and/or a screen. The screen may be a touch screen allowing both information display and user input. The programmer 32 further includes a processor 83, memory 84, and a power supply 85. The processor 83 and memory 84 can serve as control circuitry for conducting the functions described herein. The power supply 85 can be any conventional circuitry tier providing electrical energy for running the programmer 32. While a programmer 32 is provided as an example of an EMD that may utilize the methods disclosed herein, other EMD's may have similar circuitry for performing some of the same or different functions.

Implementations of the present disclosure may utilize a system of encryption, in conjunction with an authentication method or methods, in order to ensure that communications to and from communication nodes, and particularly to and from IMD 20, are legitimate and that information in signals cannot be recognized by an unauthorized device. For example, 128 bit advanced encryption standard (AES) may be used to encrypt transmissions. In certain embodiments, the legitimacy is ensured by a rigorous approach to data encryption and management of a session key.

Authentication may involve an affirmative interaction between patient 12 and a clinician (not shown) during which the clinician informs patient 12, either directly or by implication, and secures authorization to access patient 12 information, including any static data constituting sensitive information, maintained in IMD 20 and, if necessary, to interrogate and reprogram IMD 20. Authentication may ensure that the clinician does not accidentally start a data exchange session with the wrong patient or without a patient's knowledge. Authentication may require that a session key uniquely associated with IMD 20 be sent between the devices to establish a secure communication session. During authentication, IMD 20 interfaces with an external device, such as programmer 32, to either receive or share the session key assigned to IMD 20. Authentication must be completed prior to access of protected data and access to authorization of protected actions (e.g., therapy control) in various embodiments.

The following discussion provides a brief overview of exemplary session key delivery protocols. However, the description of the session key delivery protocols is merely illustrative and is not intended to limit the scope of the present disclosure. In various embodiments, a session key is stored in programmer 32 or the programmer 32 is configured to generate a session key as needed. A short range telemetric link may be provided between programmer 32 and IMD 20 using inductive telemetry to permit programmer 32 to communication with IMD 20. In an exemplary technique, programmer 32 is placed over the location of the IMD 20, and the programmer 32 sends the session key to the IMD 20 over the telemetric link to establish a secure communication session. The communication session is secure because the session key is shared between the devices, and each transmission can be coded by the session key (e.g., by a unique number of the session key) so that the receiving device knows any transmission appropriately coded is from a trusted source and that any data transmitted can only be recognized by another device having the same key.

In various embodiments, an external medical device, such as programmer 32, can generate a session key when a communication session is being established, or is about to be established, with an implanted device. The generated key can then be transmitted to the implanted device and used as a shared secret between the two devices for secure communication. In various alternative embodiments, the implanted medical device, such as IMD 20, generates the key and transmits the key to an external device, such as programmer 32.

In various embodiments, a key delivery protocol may be used to propagate the session key to another device. An authentication device, such as a smartcard (not shown) that is associated with IMD 20, may contain the IMD 20 session key. A smartcard can include embedded integrated circuits which can facilitate identification, authentication, data storage and application processing. Each smartcard can be uniquely authenticated for each patient and/or clinician, possession of the card thereby providing a physical layer of security for communicating with an IMD. In setting up a communication session, the smartcard may be physically or wirelessly coupled to a programmer interface device not shown) or directly to programmer 32. The smartcard may be issued together with the IMD 20 (and given to patient 12 after surgery), or the necessary information may be entered onto patient's 12 preexisting smartcard. After coupling the smartcard to programmer 32, for example, the session key may be transmitted to programmer 32 to initiate the communication session such as described in commonly-assigned U.S. Pat. No. 7,930,543, filed Jul. 26, 2007, which is incorporated herein by reference in its entirety. In a further embodiment, a password associated with IMD 20 may alternatively or additionally be entered to permit the propagation of the session key to programmer 32. In various embodiments, a near-field inductive signal is sent from an external medical device, such as programmer 32, to an IMD, such as IMD 20, to indicate that the patient has granted the user of the external medical device permission to access the patient's IMD by permitting the user to get sufficiently close for the inductive connection.

The programmer 32 can use the session key to encrypt and/or decrypt sensitive information, such as PHI, patient data, medical information, device settings, and/or other information within the scope of HIPAA. A suitable security scheme for implementing the various privacy and message integrity functions in a representative embodiment is the Advanced Encryption Standard ("AES"). The information is sent to and from IMD 20 and programmer 32 as encrypted information for subsequent decryption using the session key and retrieval by the receiving device. The encrypted sensitive information may be sent to IMD 20 over a telemetric link using RF telemetry.

The devices participating in a communication session will exchange information provided a valid (i.e. properly authenticated) communication session is established, the communication session remaining valid as long as the session key transferred between the devices remains active. In the context of IMD 20 and programmer 32, this information may include transmission of data sensed by IMD 20 to programmer 32 and/or transmission of therapy parameters from programmer 32 to IMD 20. Similarly, programmer 32 may retrieve encrypted sensitive information from IMD 20 and use the session key to decrypt the encrypted information into a readable state. In various embodiments, an unencrypted copy of part or all of the sensitive information may be stored on IMD 20 by programmer 32 over a wireless link. To ensure patient privacy, in some embodiments, the unencrypted sensitive information may only be retrieved from the IMD 20 over a secure wireless link. Communication actions may include commands for activation of protected actions, such as changing stimulation or other therapy parameters.

In various embodiments, the communication session between IMD 20 and programmer 32 is established by generating the session key and authenticating programmer 32 to IMD 20. The session key may be stored temporarily or permanently on either the IMD 20 or programmer 32. One or more permanently stored session keys may be maintained in a fixed location, typically on the IMD 20, but may also be stored on programmer 32 or another external device. Ephemeral session keys may be generated on an as needed basis, such as by IMD 20 for subsequent retrieval by programmer 32 using telemetry.

In various embodiments, a device includes stored protocol for generating a session key, such as an algorithm that generates a session key with a unique code using a random number generator for each time a communication session is being established. The newly generated session key is then sent to the device with which the communication session is being established. In various other embodiments, one session key is uniquely assigned to each IMD 20. For example, an IMD may be given a unique session key, the session key being unique based on a unique code, such as a number or series of letters and numbers. In various other embodiments, each programmer is given a unique session key.

A communication session can be established between two devices, such as IMD 20 and programmer 32, wherein the session key is transmitted from the IMD 20 to the programmer 32 (or vice versa), such that both parties of the communication session have the same session key, and the only session keys containing a unique shared code. Some signature of the unique code can be added to data transmissions so that the devices in a communication session may know that a particular transmission came from the other device sharing the session key. The code may also be used in encryption and decryption of data, such that only another device also having the session key can fully read the data. Part or all of patient information may be encrypted using the session key. The encrypted information may then be exchanged through telemetry. Encryption allows sensitive information to be securely transmitted over an RF or other wireless link in compliance with applicable patient health information privacy laws and regulations. The session key is subsequently used by the receiving device for decryption of the received information Upon completing authentication, IMD 20 and programmer 32 may communicate securely so long as the communication session remains active. Several criteria can be used to determine whether the session is active as discussed herein further, including periodic user input and/or data exchange. In various embodiments, a communication session may be defined as being active during the valid lifetime of the session key. In other words, during the time the session key is active, re-authentication of the session is not required and therefore not performed for communication between IMD 20 and programmer 32 or any other connected devices. In various embodiments, a communication session may be terminated following timeout of a pre-determined duration. The duration may be defined during the authentication process, or may be determined autonomously by IMD 20, and the duration might further be redefined via a secure communication request after communication has started. Responsive to a lapse of the count of the session key, the current session key may be invalidated or discarded and re-authentication of programmer 32 to IMD 20 may need to be performed in order to initiate a new session.

The telemetry session may be manually closed by the user, in which case the validity of the session key may be terminated immediately or following timeout of the predetermined duration. Following termination, no further communication of patient information can take place between IMD 20 and programmer 32 because no session key will be able to authenticate more communication between the devices. In the event that a communication link is interrupted (e.g., one of the IMD 20 or programmer 32 goes out of communication range), the telemetry communication session may be terminated immediately or following timeout of the predetermined duration. In some embodiments, communication may be temporarily paused to, among other things, minimize battery consumption (e.g., the communication session enters a hibernation mode). In such a case, the communication session may be terminated by disabling a key following a timeout of the predetermined duration, the predetermined duration set for the situation of pausing communication, and the timeout countdown may be started upon the start of the paused period, and ended when the session is un-paused or the countdown completes. The session key can then be deleted upon completion of the count, ending the secure communication session and disallowing further secure communication until a new session is established.

Figure 3:
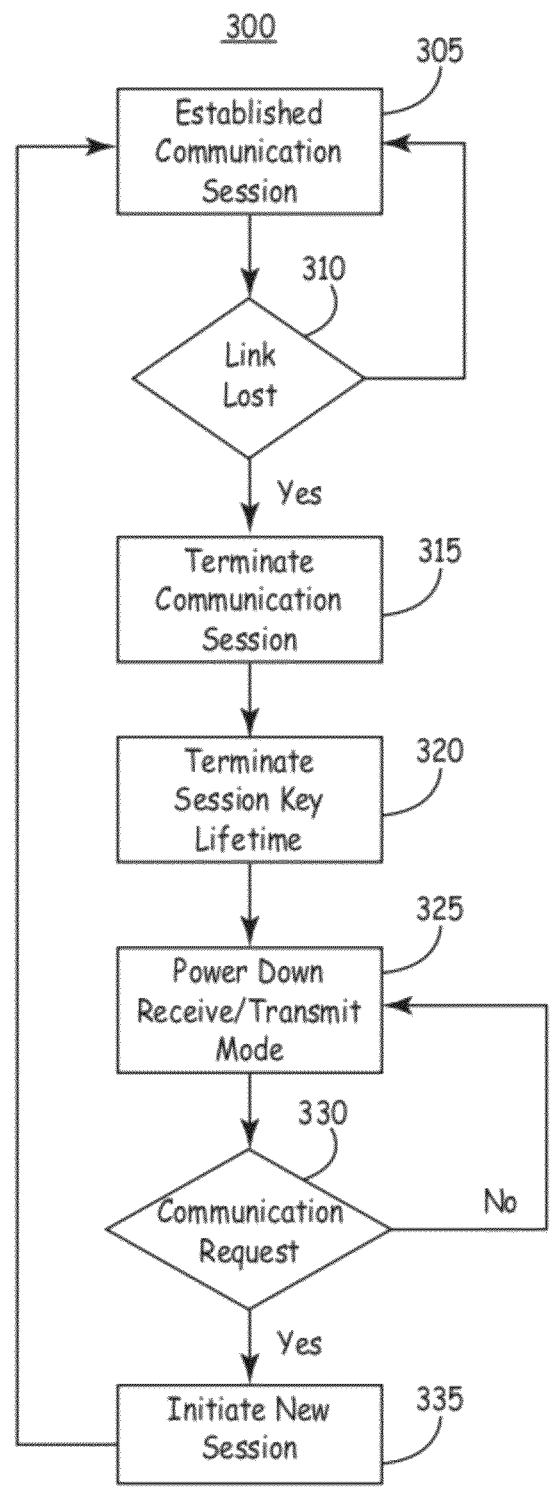
FIG. 3 is a flow diagram illustrating a method of terminating the valid lifetime of the session key of an established communication session according to an embodiment of the present disclosure.

FIG. 3 is a flow diagram illustrating a method 300 of terminating the valid lifetime of the session key of an established communication session 305 subsequent to a loss of a communication link between IMD 20 and programmer 32. An example of a scenario where the link is lost may arise, for example, in a clinical setting where a patient leaves a room, albeit for a short duration, perhaps to obtain a weight measurement. In this example, the patient travels over a distance that causes IMD 20 to go out of communication range of programmer 32. Responsive to IMD 20 going out of range, the communication link may be lost 310. Thus the communication session may be prematurely terminated 315 resulting in the session key lifetime terminating 320 prematurely. Subsequent communication 330 of information between IMD 20 and programmer 32 will require re-authentication and initiation of a new communication session 335, which may be time and energy consuming, particularly when receive/transmit circuitry is powered down 325 following termination 320 of the session key lifetime.

Figure 4:
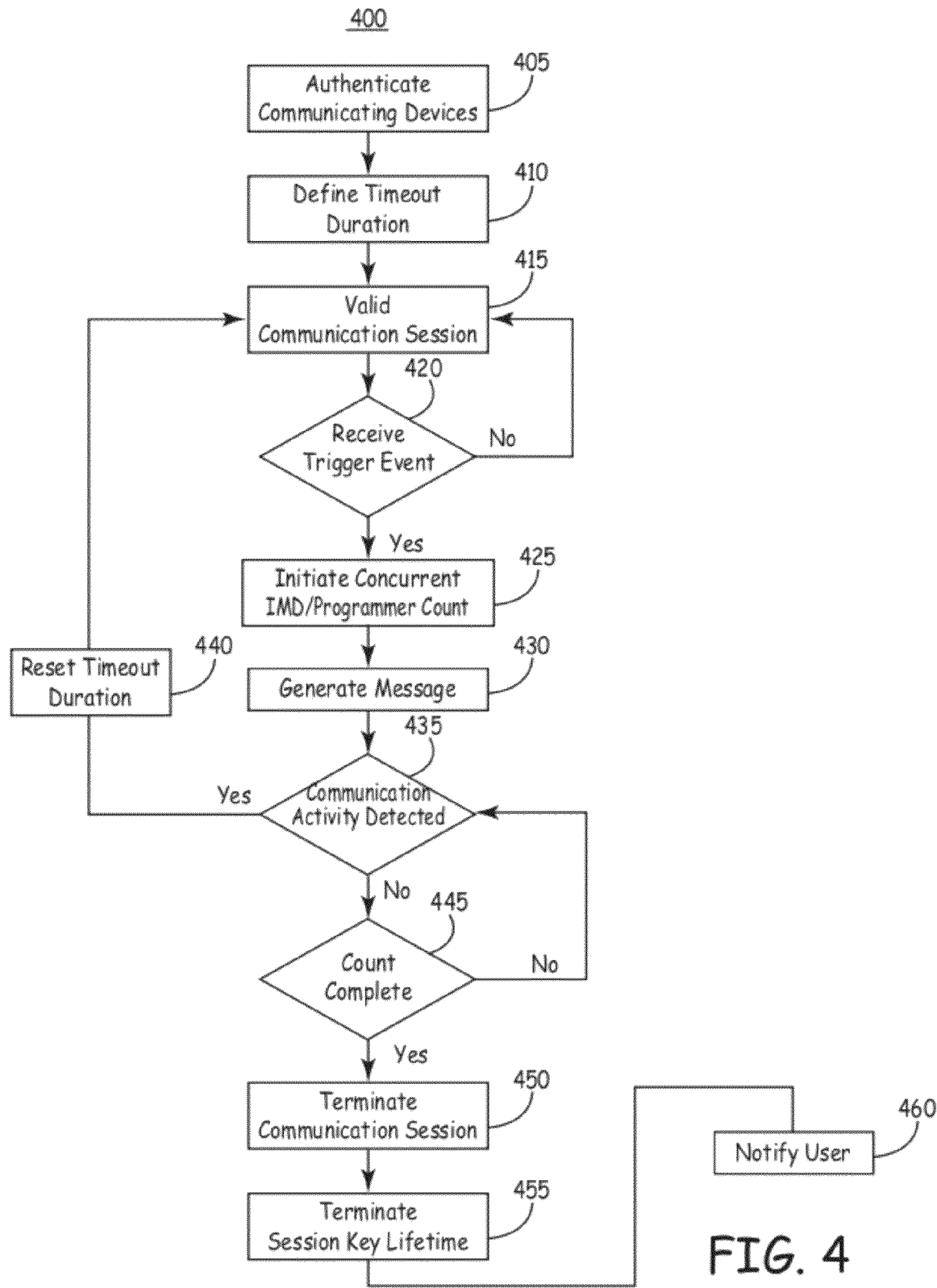
FIG. 4 is a flow diagram illustrating a method of terminating an established communication session subsequent to interruption of the communication link of an established communication session.

FIG. 4 is a flow diagram illustrating a method 400 of terminating an established communication session subsequent to interruption of the communication link between IMD 20 and programmer 32. The method 400 prevents a premature termination of the communication session by preserving the validity of the session key for a predetermined duration following a trigger event to close a communication session. A trigger event can include recognition of a loss of the communication link. As previously described, a communication session is established using authentication 405 of programmer 32 to IMD 20, authentication 405 providing some assurance that programmer 32 and IMD 20 can uniquely identify one another during a communication session and that patient information will be secure via a session key exchange.

In the method 400 of FIG. 4, a predetermined timeout duration is defined 410 by programmer 32 and communicated to IMD 20. The duration may be determined automatically by programmer 32 based on one or more inputs such as the session type. In various embodiments, programmer 32 may have a look-up table with one or more timeout durations associated with each session type. For example, an implant procedure may require a long period of time to complete and thus the timeout duration may be set to this longer period (e.g., seven hours), while a refill procedure for an implantable pump may only require several minutes (e.g., approximately thirty minutes). In deep brain stimulation, an implant procedure and programming session may take hours while follow up procedures may only take fifteen minutes. The dynamic setting of a timeout duration of a session key helps tailor and therefore minimize the vulnerability to malicious users should the communication session not be formally terminated by the friendly users.

The duration may be set automatically when a user indicates which type of procedure is planned. As such, no direct user input indicating the timeout duration is needed as the IMD and/or programmer can automatically determine an appropriate session key timeout duration. Therefore, if a user input indicates that an implant procedure is to take place, then the timeout duration can be automatically defined 410 using the longer time period of the look-up table associated with the particular type of procedure (an implant procedure per the example). The timeout durations of the lookup table may be updated automatically in response to measuring sessions over time, receiving user overrides, or adjustments from a user. In some embodiments, an IMD 20 and/or programmer 32 may learn a timeout duration based on the timing of several previous sessions or another other information that may inform heuristic learning of future timeout sessions. For example, the average of the previous 5 sessions plus a margin (e.g., 25%) can be calculated and defined 410 for the timeout duration of the next session. Average procedure durations can also be determined for each procedure type and stored in a look-up table, such that an indication of the next procedure type can trigger automatic reference to the table to determine a time out duration for the next procedure.

In various embodiments, the predetermined duration may be received from a user. Thus, the user may input the duration into programmer 32 during the authentication procedure 405 and this duration may be transmitted to IMD 20. Overrides to the user input duration may be permitted during the communication session. In yet another example, the duration may be a time interval that is preprogrammed in IMD 20 or programmer 32.

The session key may then be transmitted to IMD 20 by programmer 32 and a valid communication session established 415. Responsive to receiving 420 an indication of the occurrence of one or more of a plurality of preprogrammed trigger events/conditions 600, a count of the predetermined duration may be performed 425. The count may either be a count down or a count up. The count of the predetermined duration may be performed and enforced by one or both of IMD 20 and programmer 32.

Prior to, during, or after the performance of the count 425, a message may be generated 430 by programmer 32 and provided to the user to inform the user that the count is in process. The message may be a visual notification, an auditory notification, a vibratory notification or any other known type of notification. This message may indicate to a user that the authenticated communication session 415 will end following a period of time if certain criteria are not met, such as bringing the devices within communication range and/or actively using the programmer 32. This notification may be generated by an EMD and/or IMD. For example, if a patient leaves the room during a programming session and is not aware that he or she needs to return in 15 minutes (corresponding to a 15 minute timeout duration) the device may vibrate or initiate some other alert within the 15 minutes (e.g., at ten minutes) in an effort to get the patient to return before the session is closed by timeout.

IMD 20 and/or programmer 32 may periodically determine 435 whether any activity is present that requires a valid communication session. The activity may include commands generated by the user or programmer 32, communication from programmer 32 to IMD 20 or any other telemetry related activity between IMD 20 and programmer 32 indicative of continuing communication. Count 425 may be reset 440 responsive to the occurrence of activity at any time during performance 420 of the count. Upon reset 440, IMD 20 and programmer 32 will remain in the established communication session 415 until another indication of the occurrence of one or more of a plurality of preprogrammed trigger events/conditions is received 420.

If, however, no communication activity is detected 435 during the count duration and the count is completed 445, the communication session is terminated 450. The session key may be invalidated upon completion of the count by terminating 455 the session key lifetime. In addition, an indication 460 may be provided to the user notifying the user that the communication session has been terminated 450. This indication may be a visual notification, an auditory notification, a vibratory notification or any other type of notification.

Figure 5:
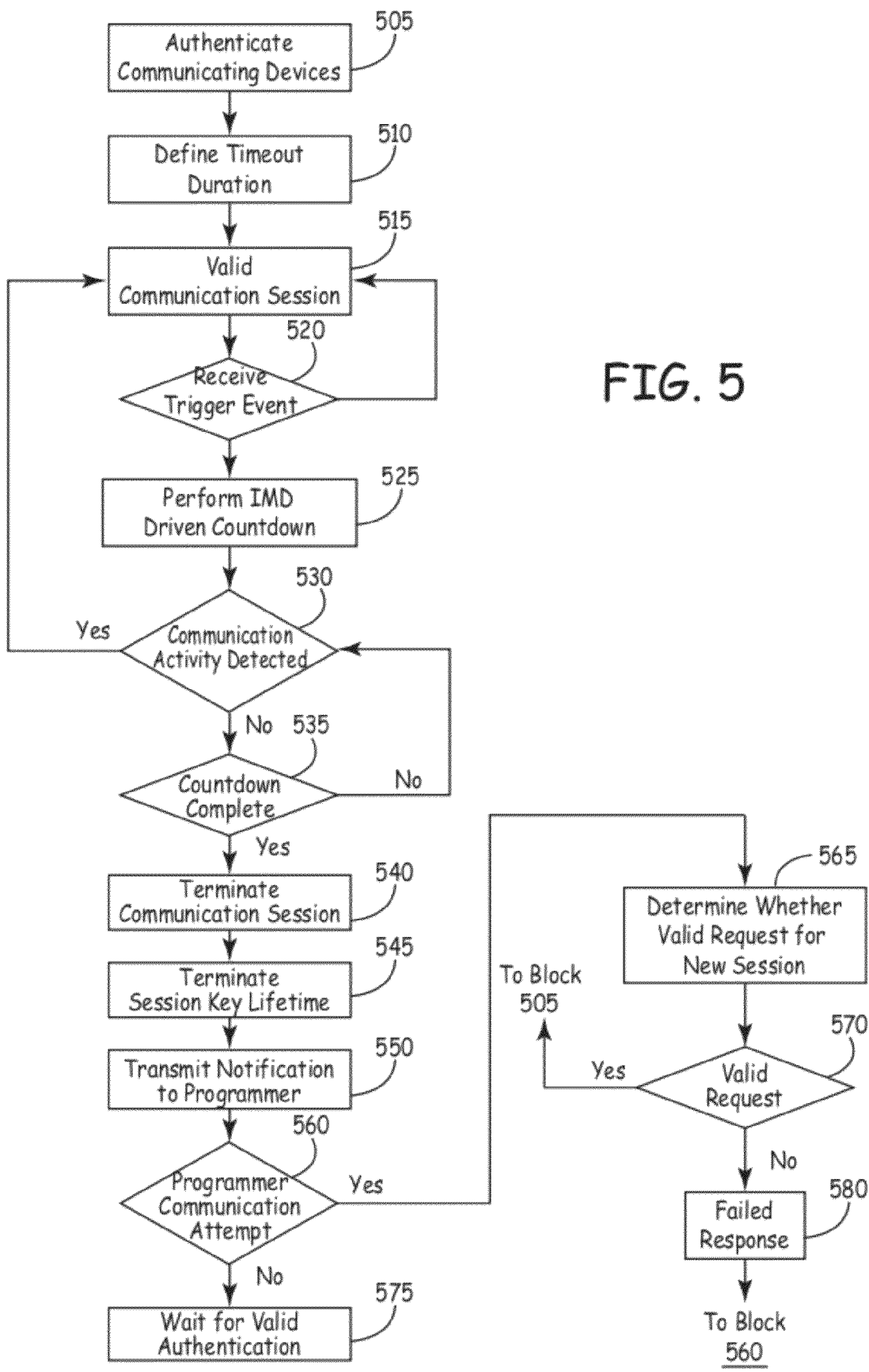
FIG. 5 is a flow diagram illustrating another alternative method of terminating an established communication session subsequent to interruption of the communication link of an established communication session.

FIG. 5 is a flow diagram illustrating another method 500 of terminating a communication session subsequent to interruption of the communication link between IMD 20 and programmer 32. Authentication 505 of programmer 32 to IMD 20 is initiated to establish a communication session. A predetermined timeout duration may be defined 510 by programmer 32 and communicated to IMD 20. Alternatively, IMD 20 may define 510 the timeout duration based on one or more criteria, such as the duration of prior procedures and information communicated by programmer 32. The session key may then be transmitted by IMD 20 to programmer 32 to establish 515 a valid communication session.

Responsive to receiving 520 an indication of the occurrence of one or more of a plurality of preprogrammed trigger events/conditions, a count 525 of the predetermined duration may be initiated. The count 525 may either be a count down or count up. IMD 20 may periodically determine whether any activity is present 530 that indicates a valid communication request.

In various embodiments, count may be performed 525 by one or both of the programmer 32 and the IMD 20. By way of illustration and not limitation, count is illustrated as being performed 525 by IMD 20. IMD 20 determines 510 a predefined timeout duration. The parameters fir defining 510 the timeout duration may be preprogrammed into the IMD 20, calculated by IMD 20 based on predefined criteria, such as described in FIG. 4 or elsewhere herein, or may be received from an external device such as programmer 32.

Performance of the count 525 may be terminated in response to detection 530 of activity at any time during the count. Following such termination, the IMD 20 and programmer 32 will remain in the established communication session 515 until another countdown completes 535 without detection 530 of communication activity. Count 525 of the timeout duration may resume from the remaining time duration in a subsequent count.

Responsive to the completion 535 of count 525, the communication session is terminated 540. In various embodiments, a signal may be transmitted 550 to programmer 32, prior to or upon completion 535 of count, indicating that the communication session has been terminated. Alternatively, to conserve the power and resources of IMD 20, the communication session may be terminated 540 upon completion 535 of count. In other words, the IMD 20 may invalidate the current session key lifetime 545 following termination 540 of the communication session. Upon a subsequent attempt 560 by programmer 32 to communicate with IMD 20, IMD 20 determines 565 whether a valid re authentication and initiation of a newly authenticated communication session 505 has been successfully performed. In the absence of the new communication session, IMD 20 waits 575 for a valid authentication and initiation of a new communication session. Additionally, IMD 20 may send a failed response 580 indicating that the session key has failed. If a valid request for the new session is identified 570, then the communicating devices are authenticated 505.

In some embodiments, a key can automatically be disabled when a new key from another device is received. For example, if a patient is in a first room having his or her IMD programmed with a first programmer, a secure communication session may be established by the first programmer sending the IMD a first session key, as described herein. Then the patient may go to another room for programming with a second programmer while the first session and first session key are still active. In some embodiments, the first session key will be disabled (e.g., deleted) when the second programmer established a second communication session with the IMD by sending a second session key. In some embodiments, a first valid communication session based on a first session key will prevent a second communication session from being established with the same IMD until the first valid communication session ends (e.g., the first session key is disabled).

Figure 6:
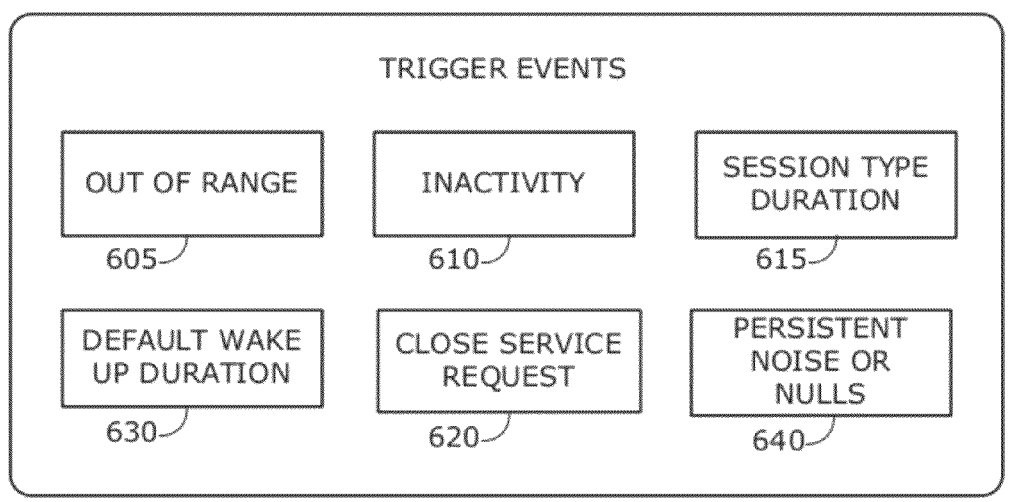
FIG. 6 depicts exemplary preprogrammed trigger events that may trigger the termination of a communication session.

FIG. 6 depicts exemplary preprogrammed trigger events 600 that may trigger the start of counting leading to termination of a communication session. An out-of-range 605 event may arise when the physical separation between communicating devices results in a telemetry signal becoming diminished to thereby prevent the devices from communicating. For example, a device communicating under the Medical implant Communication Service (MICS) frequency band with an RF frequency centered between 401 MHz to 406 MHz may have a range of up to 15 meters. Those skilled in the art will recognize that this range is merely exemplary and will vary due to any one of conditions such as implant depth, physical obstructions between devices, and other conditions influencing transmission distance. As an example, if the distance between the devices in the example exceeds the bounds of reliable communication (e.g., 15 meters), the telemetry signal strength is greatly diminished and may result in a loss of the link. The telemetry signal may also be affected by physical obstacles, such as walls, between the devices. Accordingly, out-of-range 605 event may arise due to any one of several known situations that attenuate the telemetry signal and result in a loss of communication.

An inactivity 610 event may arise following a lapse of a preprogrammed period of user inactivity, or any inactivity. The preprogrammed user inactivity duration may be defined in accordance with the techniques described herein for the timeout duration. In an alternative embodiment, programmer 32 or IMD 20 may "learn" user patterns to derive the inactivity patterns and durations. In an example, a duration between each successive command may be determined for a predetermined period and an average time calculated to obtain the inactivity duration.

A session type 615 event may also trigger the start of a session timeout duration, the expiration of which terminates the communication session. Preprogrammed durations associated with each type of communication session may be defined and stored in programmer 32 or IMD 20. A user may then be prompted, for example, during the initialization procedure, to specify the activity to be performed or the anticipated duration fur the session. The session duration may then be used to determine when the communication session is expected to end, thus triggering termination of the session.

A close service request 620 may also trigger termination of the communication session. Upon completion of device related activity, a user may initiate the session close procedure and this may be used as a trigger.

In a further example, a communication session may be terminated following expiration of a timeout duration which was started based on an interruption from a non-connected device, such as an EMD. In this example, a non-connected EMD may be a device that does not currently have a communication session established with the IMD 20. The interruption may be in the form of an attempt by the non-connected EMD to initiate a new communication session with the IMD 20. In some cases, a secure and valid far-field communication session (e.g., using RF communication spanning many feet) with a first EMD can be ended (e.g., by invalidating a session key of the far-field communication session) based on a near-field communication (e.g., using inductance communication spanning only a few inches) from a second EMD. In such a case, the nature of the near-field communication can provide a measure of assurance that the patient or other user intends that the interaction with the much closer second EMD takes priority over the first EMD. Also, if confusion exists as to which of two or more programmers are communicating with an IMD, brining one of the programmers into near-field range can cause the IMD to disable any session key not associated with the programmer in the near-field range, where the communication session will either persist or end and thereby settle which programmer is (or was) communicating with the IMD.

In addition to terminating an already established communication session, a default wake-up duration 630 may be provided during the process of establishing the communication session. A count of the wake-up duration 630 may be performed to terminate the process of establishing a communication session and thereby invalidate the associated session key. In other words, if the process of establishing a communication session takes longer than the wake-up duration 630, this may indicate an anomaly in the establishment process and thus further action would be impeded by the termination. The wake-up duration 630 may be a fixed duration that is pre-programmed in IMD 20 and utilized during establishment of the communication session. The wake-up duration may be factory programmed based on user guidelines indicating a generally acceptable duration for establishing a communication session. In an exemplary embodiment, the wake-up duration 630 may be on the order of about two minutes. In some cases, if an IMD does not receive a valid encrypted message within a predetermined amount of time after a secure communication session is first established, the IMD may delete or otherwise invalidate a session key transmitted by the EMD upon which the secure communication session is based. This predetermined amount of time may be relatively short (e.g., a few seconds) and different from other timeouts based on inactivity or lack of communication because the predetermined amount of time begins from the start of the communication session and lack of communication following the initial establishment of the valid communication session may indicate an error in establishing the session.

In various embodiments, persistent noise or nulls 640 may trigger the start of a session timeout duration, the expiration of which terminates the communication session. In some cases, if the nulls cease or the communication noise ends, then the timeout can be cleared and the valid session can continue.

In some embodiments, entering a hibernation or sleep mode starts a countdown timer which can terminate a communication session as discussed herein. A hibernation or sleep mode can put communications circuitry, as well as other circuitry, into a standby mode whereby power consumption is decreased. A hibernation or sleep mode may be entered when an indication is made on a programmer, for example. A user may provide an input indicating a desire to enter into a hibernation or sleep mode to save battery life of the IMD when the clinician knows that communication will not be needed for some time, such as when a break is taken. Inactivity can also trigger a hibernation or sleep mode in various embodiments.

In some embodiments, a device having a permanent far-field communication session with an IMD (e.g., a patient programmer) may be temporarily blocked from using some or all communication functions if a secure communication session with another EMD based a session key is currently active. For example, if a patient attempts to communicate with his or her IMD while the IMD currently has a session key from a clinician programmer supporting a valid communication session, the IMD may communicate with the patient programmer that another session is active and the patient programmer may display an indication of the other session. In some cases, the IMD may communicate the session timeout duration or other information to the patient programmer, which might also be displayed on the patient programmer to indicate to the patient when it might be useful to retry communicating with the IMD via the patient programmer.

Figure 7:
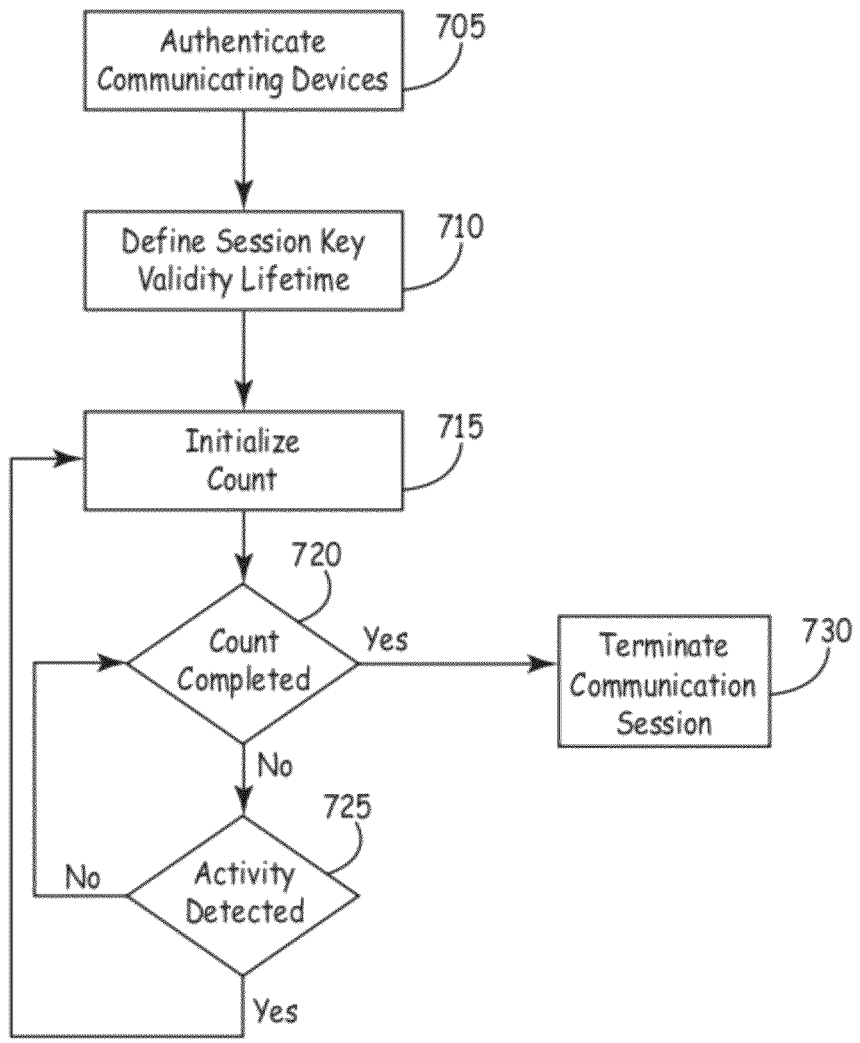
FIG. 7 is a flowchart illustrating a method for configuring the validation lifetime of a session key.

FIG. 7 illustrates a flowchart of a method 700 for configuring the validation lifetime of a session key. Communicating devices can he authenticated 705 to each other, such as programmer 32 to IMD 20, to establish a communication session, as described herein. During the communication establishment process, a session lifetime duration is defined at 710. The session lifetime duration may refer to the duration between successive communication sessions. The session lifetime duration may be provided by a user or determined by the programmer 32 or IMD 20 based on the session type or any other criteria. A count of the session lifetime duration is initialized 715 subsequent to the successful establishment of a communication session. Therefore, the session key can remain active tier the duration of the session lifetime duration and the communication session may be terminated 730 upon expiration 720 of the count of the session lifetime duration. User or device activity detected 725 during the session lifetime duration reinitializes 715 the session lifetime duration. In other words, the session lifetime duration of the session key is refreshed and restarted with one or more successive communications between the devices.

In various embodiments, aspects of the exemplary flowcharts illustrated above may be combined into a single algorithm. For example, FIG. 5 may be modified to include the generation of a message 430 of FIG. 4 subsequent to initiating the count 525. In another example, the timeout duration may be reset 440 (FIG. 4) upon detection 530 of activity (FIG. 5). Such modifications can also include FIGS. 8 and 9, as well as all other embodiments disclosure herein.

Figure 8:
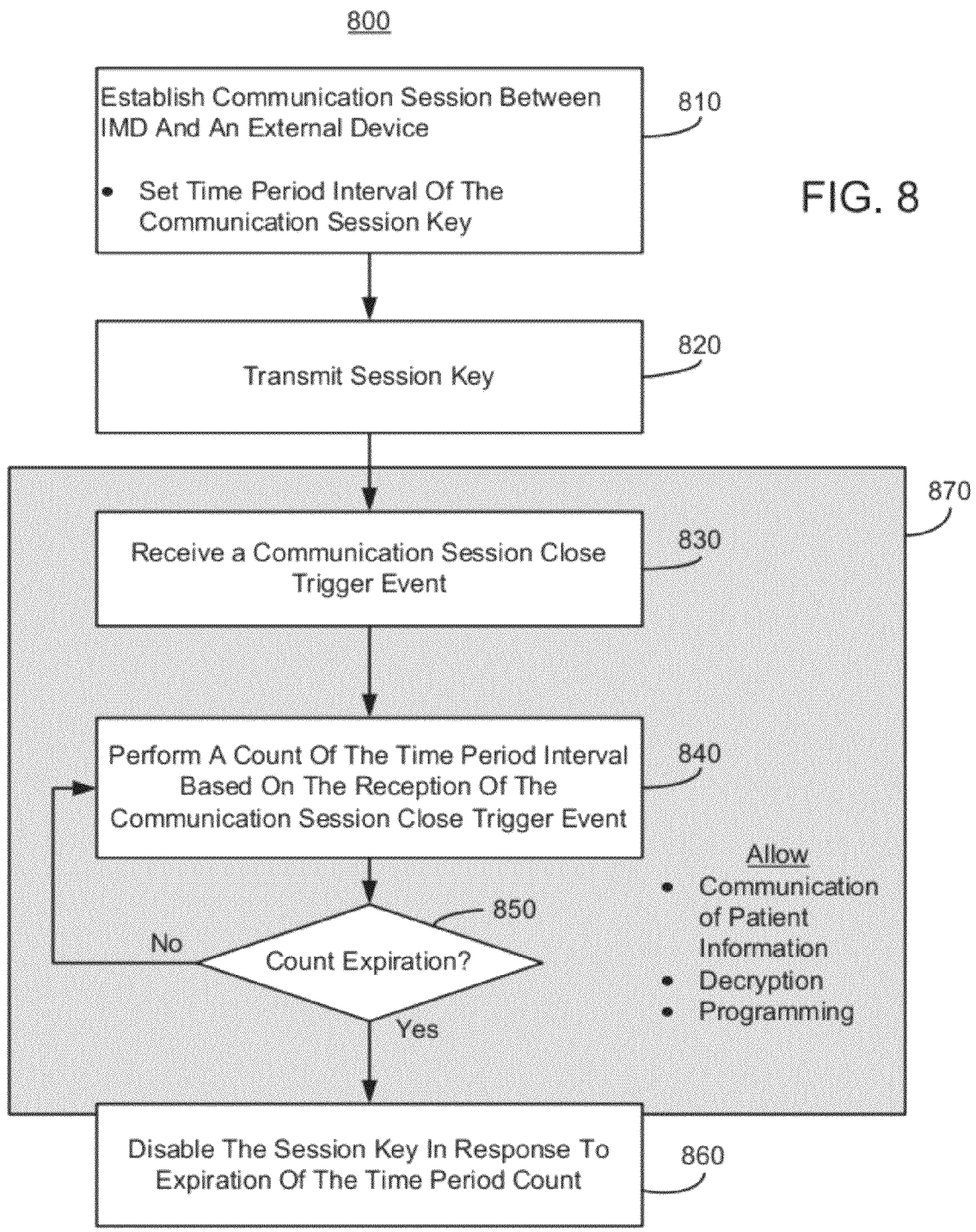
FIG. 8 is a flowchart illustrating a method for configuring the validation lifetime of a session key.

FIG. 8 illustrates a flow chart demonstrating various aspects of the present disclosure. The method 800 of FIG. 8 includes establishing 810 a communication session between an IMD and an external device, which can include the steps of authentication as discussed herein. Such devices could be any of the implantable and external devices discussed herein, including IMD 20 and programmer 32. A communication session, as used herein, refers to a period of information exchange between two or more devices. Such a communication session may start out insecure, insecure in that a security protocol has not yet been established between the devices and only one or more basic communication protocols are available between the devices. Such establishment 810 of a communication session may include deciding between the two devices which type of wireless communication protocol to use and setting parameters for communication. A communication session may be composed of continuous or intermittent wireless exchanges between two or more devices.

In some embodiments of the present disclosure, establishing 810 the communication session includes setting a time period interval of a session key. Setting the time period may be performed by the IMD or programmer after the IMD or programmer recognizes with which type of device it is establishing 810 communication. For example, recognition of the type of device that an is establishing 810 communication with may be suggestive of the nature of the communication that will likely take place during the communication session, and this information could be used to set the time period interval. Continuing with the example, if the IMD recognizes that the type of device it is establishing 810 a communication session with is strictly a data collection device, then the IMD can set a certain time period appropriate for the transfer of data, which might be expected to have a rather continuous transaction and therefore have a relatively short timeout duration for inactivity. However, if the IMD recognizes that the type of device with which it is establishing 810 a communication session is a programmer capable of testing and reprogramming the IMD, then a longer time interval may be set because longer periods of inactivity in communication can be expected while different settings are tested and evaluated. As such, the time period interval of a session key may be set by an (or other device) based on identification of which type of device with which the is establishing 810 a communication session.

The method 800 can further include transmitting 820 the session key. If the session key originated with the IMD then the session key is transmitted 820 from the IMD to the external device. In some other embodiments, the session key originated with the programmer and is transmitted 820 to the IMD. In some embodiments, the session key remains on one device but the particular set time period interval is transmitted and the time period interval of the session key is set following reception of the transmitted set time period. In some embodiments, the transmission 820 of the session key may be a part of the establishment 810 of the communication session. In various embodiments, the communication session may only be preliminary established 810 pending transmission of the session key between the devices, whereby only limited and basic communication can take place between the devices before the session key is transmitted 820.

Secure communication block 870 (indicated by shading) outlines those steps of the method 800 in which the communication session is considered secure. The communication session is secure as long as the session key has not been disabled 860. In various embodiments, certain actions can only take place when the communication session is secure. For example, in some embodiments, patient information can only be communicated when the communication session is secure. In some embodiments, decryption of transmitted information can only take place when the communication session is secure, and the session is secure only for as long as the session key is active (i.e. not having been disabled 860). In some embodiments, programming of the IMD can only take place when the communication session is secure, such as changing therapy parameters or implementing testing protocol (e.g., induction of defibrillation or stopping components from operating).

Within the secure communication session block 870, the IMD and/or other communicating device can receive 830 a communication session close trigger event. A communication session close trigger event can take several forms, including a loss of communication between the devices (e.g., one device moved beyond the communication range of the device(s)), degradation of communication (e.g., low quality signal is detected), communication inactivity (e.g., no unilateral or bilateral communication), the close of a certain program (e.g., a reprogramming application on a programmer), absence of substantive information exchange (e.g., no patient information or programming instruction exchange), and/or sonic other event indicative of an intention to stop, or an inability to effectively continue, the communication session. Such triggers can be any of those listed or described in association with FIG. 6 or elsewhere herein, for example. In some embodiments, the communication session close trigger event is generated on one device (e.g., the IMD) and then is transmitted to the other device of the communication session, where the other device then receives 830 the communication session close event. In some embodiments, the communication session close trigger event is received 830 by a processor after being generated in the same device. For example, communication circuitry may generate the close trigger event indicating a loss of communication or communication inactivity between the devices of the communication session. Other circuitry components that may generate a close trigger event include power circuitry (e.g., indicating low power or loss or power), user controls (e.g., indicating a user input for termination of data transfer, programming, or transcutaneous communication), integrity circuitry (e.g., indicating a malfunction or other error), and/or security circuitry (e.g., indicating a possible breach of data security or hack).

Reception 830 of a communication session close trigger event can lead to disablement 860 of the session key and loss of the secure 870 communication session. Users will eventually intend to close the communication session and protect patient information and IMD access by disabling the session key 860. However, inadvertent disablement of the session key can be frustrating as authentication steps would have to be repeated to get to the point where the clinician was before the inadvertent disablement 860 of the session key. As such, the method 800 includes several steps, as do other embodiments described herein, to make the communication session robust while balancing security concerns.

According to the method 800 of FIG. 8, a count of the time period interval is performed 840 based on the reception 830 of the communication session close trigger event. Such a count can be a count up, down, or any other technique for tolling a period. As long as the count has not expired 850, secure communication is allowed (e.g., as shown by block 870). However, if it is recognized that the count has expired 850, then the session key is disabled 860. Disablement 860 of the session key ends secure communication. Disablement 860 of the session key may end all communication between the devices, or only certain functions may be disabled, such as communication of patent information, decryption, and/or programming of the IMD.

In some embodiments, the performance 840 of the count of the time period interval may be reset if one or more criteria are met. For example, if the communication session close trigger event concerns loss of communication or communication activity, then the count can be reset with each communication of data.

User input into a programmer can also reset the count in various embodiments, thereby allowing expiration 850 if the user of the programmer fails to maintain use of the programmer (e.g., if the clinician goes 2 minutes without inputting or otherwise affirmatively interfacing with the programmer). Such a feature can be useful in a situation where the clinician neglects to formally close out of a programming session programming a first IMD and puts the programmer down for a period of time. If the clinician then picks up the programmer and intends to program a second IMD, the input instructions will not program the first IMD accidently so long as the count has expired 850 because the session key enabling programming will have been disabled 860.

In various embodiments, the initial steps (e.g., 810 and 820) to obtain the secure 870 communication session may require a password or some other authentication step (e.g., by use of a smart card or a proximal near-field inductive communication). Therefore, if a communication session is prematurely closed, then these same authentication steps would have to be repeated. However, the method 800 provides a way for recovering a communication session following reception 830 of a communication session close event without necessarily terminating secure 870 communication. Such a robust secure 870 communication session may be more user friendly by requiring fewer submissions of authenticating information while preserving secure communication, although not indefinitely preserving the secure communication. As demonstrated in block 870, secure communication can continue so long as a count has not expired 850 following reception 830 of a communication session close trigger event.

Figure 9:
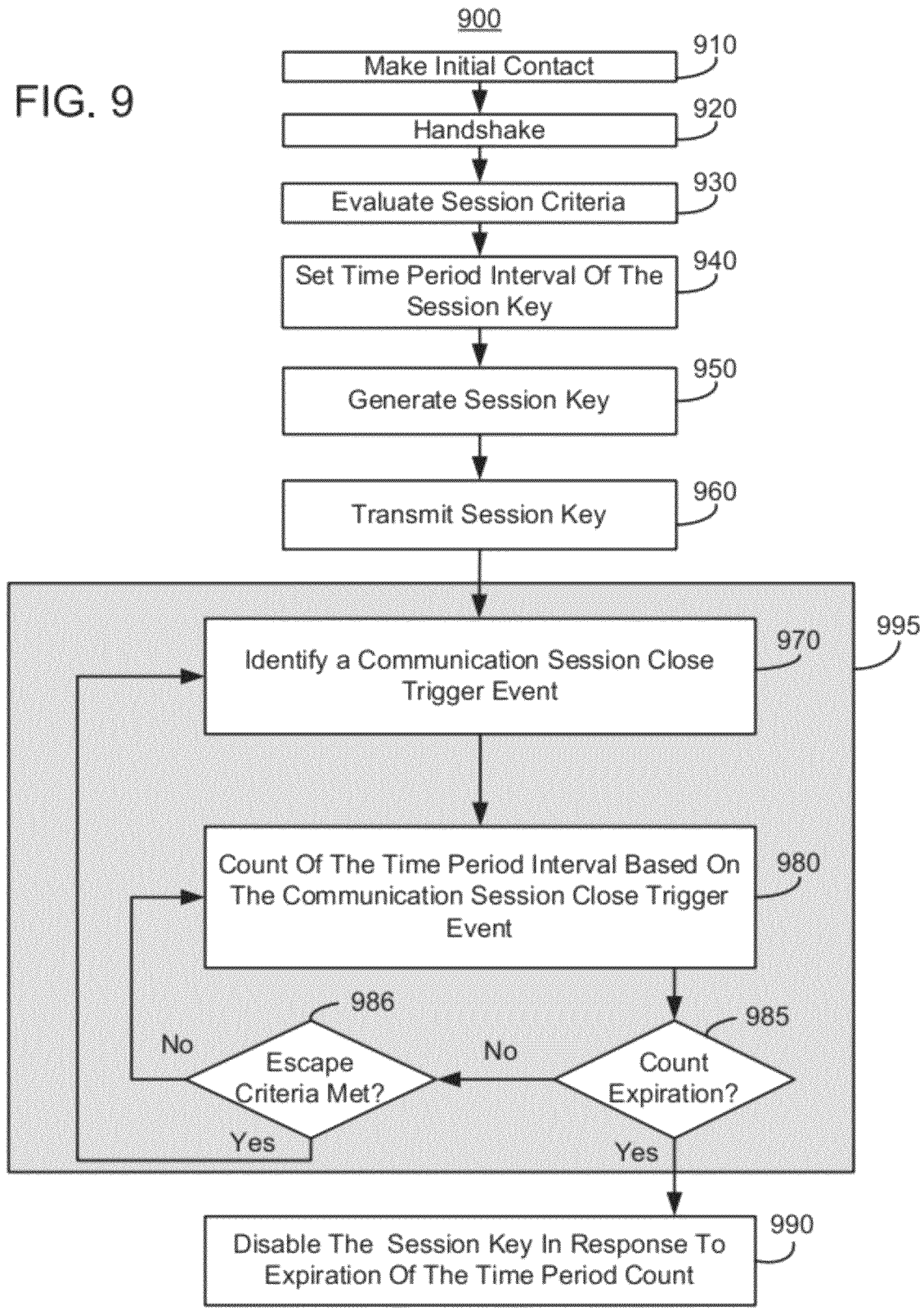
FIG. 9 is a flowchart illustrating a method for configuring the validation lifetime of a session key.

FIG. 9 illustrates a method 900 demonstrating various aspects of the present disclosure. The method 900 includes making 910 an initial contact between an implanted device (e.g., IMD 20) and an external device, such as a programmer (e.g., programmer 32). The initial contact can include a programmer sending an initial signal to wake up, ping, or otherwise reach out to the implanted device to cause the implanted device to respond.

An initial contact can begin a process of handshaking 920. Handshaking can be an automated process of negotiation between communication devices that sets parameters of a communication channel established between two entities before normal communication over the channel begins. Because handshaking sets basic communication parameters that are acceptable to circuitry at both ends of the communication channel, it precedes normal information transfer (e.g., the transfer of patient information). Handshaking can set, among other things, information transfer rate, coding alphabet, parity, interrupt procedure, and other protocol or hardware features. It is noted that handshaking 920, or at least bi-directional handshaking, may not be used in all embodiments. For example, an external programmer may communicate information to an implanted device unidirectionally with a near-field link. The external programmer may determine that communication is being established (i.e. an inductance link is being established).

Before, following, or simultaneous with handshaking 920, session criteria can be evaluated 930. Such evaluation 930 can concern determining what activities are planned to occur, or are likely to occur, during the secure communication session. Criteria can include the type of devices involved with the communication session. In some cases, evaluation 930 of the session criteria comprises selecting which one of a plurality of different devices the IMD is establishing a communication session. For example, an implanted device may identify the type of external device with which it is in communication and recognize that the external device accepts data but is not a programmer (or may alternatively recognize the other device as a programmer). In another example, an external programmer may identify the type of implanted device with which it is in communication and recognize that the implanted device accepts programming commands but that data transfer is not supported. In some embodiments, a user may select certain programming features via an interface indicating which programming actions are planned, and the programmer and/or IMD may evaluate 930 this criteria. Such evaluation can include sending an indicator of a device model type between the communicating devices and then looking up the capabilities of the other device in a stored table.

The evaluation 930 can then be used to set 940 a time period interval of a session key. In various embodiments, the time period may be set for different lengths depending on the type of device in communication. Continuing with above example, if the implanted device recognizes that it is communicating with a device that essentially only accepts data, then the time period may be set to a relatively short interval, based on an expectation of a continuous data transfer with few and short, if any, cessations in data transfer. Alternatively, if the external device is recognized as a programmer, then the time interval may be set for a relatively longer period of time, allowing for more flexibility during the communication session, which may be required if the clinician and patient are experimenting with therapy or other parameters. Other types of session criteria are contemplated within the scope of the present disclosure, including any criteria relevant to characterizing a subsequent communication session. The time period interval can then be dynamically set 940 for a session key by control circuitry based on which out of a plurality of different external devices the IMD is establishing a communication session.

In some embodiments, a programmer or other external device may present a user with a question on an interface regarding the nature of an interaction when the session is being established or when the user is preparing the external device to make contact 910 with the implanted device. Such an inquiry may be a question presented on a display of the programmer asking whether the session is for data transfer or programming, for example. The inquiry may be asked automatically when the user attempts to establish a communication session, such as by navigating to a communication session menu in a program of the programmer. Different time period intervals can then be indexed for the different answer options, such as 1 minute for a data transfer session and 10 minutes for a programming session. The time period interval can then be dynamically set 940 for a session key by control circuitry based on any user indications (e.g., answers), which can balance flexibility and security for a plurality of different types of communication sessions.

In various embodiments, a programmer used in a number of communication sessions for different patients may heuristically learn how long communication sessions usually last depending on which type of IMD the programmer is communicating with, such as by tracking session length for a plurality of previous sessions and averaging (or other aggregating calculation) the duration for each of the plurality of different IMD's. Depending on with which type of IMD the programming is starting to communicating, the programmer can set 940 a time period interval based on the average communication session duration for that type of device. Other time intervals and conditions can be tracked by a programmer over a plurality of communication sessions and the programmer can calculate a timeout duration based on an aggregate calculation (e.g., average) of the plurality of communication sessions. For example, a programmer can track periods of inactivity where activity was resumed for a plurality of sessions. A timeout duration for inactivity can then be set based on the average of the plurality of sessions (e.g., the average plus 20%). A programmer can track periods of no communication between the devices where communication was eventually resumed for a plurality of sessions. A timeout duration for loss of communication can then be set based on the average of the plurality of sessions (e.g., the average plus 20%). Such a process can be used for calculating any type of timeout duration.

A session key can be generated 950 using the set 940 time period, or a previously generated 950 user key may be programmed with the set 940 time period. The session key may be generated 950 by the implanted device or the programmer, for example. Key generation 950 may include duplicating a key already stored or the creation of a new key. The key may include one or more codes and/or programs that can be used to authenticate devices, authenticate transmissions, and/or facilitate data encryption/decryption.

Once generated 950, the session key may be transmitted 960 between the devices, such as transmission of the key from the implanted device to an external device or from the external device to the implanted device. The external device may be the device with which the initial contact was made 910 and for which handshaking 920 and criteria evaluation 930 took place. A secure communication session (shown by shaded block 995) can take place when the key is shared between the device (e.g., when the external device or implanted device has the session key, depending on which device sent the key). The order of steps 930-960 may be different in various embodiments. For example, in some cases a session key is generated 950 and then a time period interval of the session key is set 940. In some cases, a session key is transmitted 960 (e.g., from an EMD to an IMD) and then a time period interval of the session key is set 940 (e.g., by the IMD).

Possession of the session key in the method 900 may allow any of the functions described herein, including decryption of patient information and/or programming of the implanted device, in various embodiments. Such functions of the secure communication session can take place only so long as the method 900 is performing the activities within shaded block 995 (i.e. the session key has not been disabled 990 by timeout or other invalidating event).

Identification 970 of a communication session close trigger event in the method 900 can include any trigger events referenced herein, including loss or communication and/or inactivity. A count 980 of the time period interval is begun based on the communication session close trigger event identification 970. Such triggers can be any of those listed or described in association with FIG. 6 or elsewhere herein. If escape criteria is met 986 before expiration 985 of the count, then the secure communication session can continue by waiting until the next identification 970 of a communication session close trigger event. However, if the count expires 985 (e.g., reaches zero or some other threshold), then the secure 995 communication session is ended by disabling 990 the session key.

The satisfaction of the escape criteria can end a current count 980 and stop the loop of counting down until another communication session close trigger event is identified 970. An evaluation of escape criteria can take place in association with the check to determine whether the escape criterion is met 986. Escape criteria can take several forms, such as reestablishment of communication, user input activity, issuance of a program instruction, and/or resolution of a program or hardware fault. In various embodiments, the escape criteria relate to the particular communication session dose trigger event that was identified 970 and for which the present count 980 is based. For example, if loss of communication was the communication session close trigger event, then reestablishment of communication can be the escape criteria. Moreover, if input inactivity was the communication session close trigger event, then input activity (or sustained activity) can be the escape criteria. Also, if cessation of patient information transfer between the devices was the communication session close trigger event, then resumption of patient information transfer between the devices can be the escape criteria. As such, the escape criteria can be an indication of resolution of the communication session close trigger event, the resolution indicating a user intention to continue the secure communication session.

It is noted that in various embodiments the timeout durations disclosed above may be adjusted at any time prior to conclusion of the count to either increase or decrement the timeout duration as desired during an established communication session.

Disablement 990 in the method 900 and elsewhere herein may refer to erasure of the session key, invalidation of the session key, or removal (e.g., return to the transmitting 960 device) of the session key. As such, disablement refers to any step whereby the session key is no longer available on one or both devices for securing and allowing certain activities of the present communication session.

In various embodiments, the session key is fixed except for the time period interval which may be dynamically set as discussed herein. The session key may be fixed in this way such that the session key remains the same (i.e. unique identification, securing, and encoding properties) and can be used for multiple communication sessions and for communication sessions with different devices, for which the only changing aspect of the key is that the time period interval is changed for each communication session based on criteria evaluated for each communication session. In some embodiments, the session key can have a time varying element that prevents replays of previously commanded requests from being serviced later during the session or subsequent sessions, such as disallowing tests that have already been performed or commands that have already been given.

The techniques described in this disclosure, including those of FIGS. 1-9 and those attributed to programmer, IMD, EMD, processor, and/or control circuitry, or various constituent components, may be implemented wholly or at least in part, in hardware, software, firmware or any combination thereof. A processor, as used herein, refers to any number and/or combination of a microprocessor, a digital signal processor (DSP), an application specific integrated circuit (ASIC), a field-programmable gate array (FPGA), microcontroller, discrete logic circuitry, processing chip, gate arrays, and/or any other equivalent integrated or discrete logic circuitry. "Control circuitry" as used herein refers to at least one of the foregoing logic circuitry as a processor, alone or in combination with other circuitry, such as memory or other physical medium for storing instructions, as needed to carry about specified functions (e.g., processor and memory having stored program instructions executable by the processor for determining a valid lifetime of an ephemeral session key). The functions referenced herein and those functions of FIGS. 1-9, may be embodied as firmware, hardware, software or any combination thereof as part of control circuitry specifically configured (e.g., with programming) to carry out those functions, such as in means for performing the functions referenced herein. The steps described herein may be performed by a single processing component or multiple processing components, the latter of which may be distributed amongst different coordinating devices (e.g., an IMD and an external programmer). In this way, control circuitry may be distributed between multiple devices, including an implantable medical device and an external medical device in various systems. In addition, any of the described units, modules, or components may be implemented together or separately as discrete but interoperable logic devices of control circuitry. Depiction of different features as modules or units is intended to highlight different functional aspects and does not necessarily imply that such modules or units must be realized by separate hardware or software components and/or by a single device. Rather, functionality associated with one or more module or units, as part of control circuitry, may be performed by separate hardware or software components, or integrated within common or separate hardware or software components of the control circuitry.

When implemented in software, the functionality ascribed to the systems, devices and control circuitry described in this disclosure may be embodied as instructions on a physically embodied computer-readable medium such as RAM, ROM, NVRAM, EEPROM, FLASH memory, magnetic data storage media, optical data storage media, or the like, the medium being physically embodied in that it is not a carrier wave, as part of control circuitry. The instructions may be executed to support one or more aspects of the functionality described in this disclosure.

Exemplary embodiments for adaptively configuring the validation lifetime of a session key used for securing communication with an implantable medical device have been described. These embodiments are intended to be exemplary and not limiting. For example, although the disclosure has been illustrated in the context of a deep brain stimulation implantable medical device, embodiments of the disclosure can be implemented in other implantable devices such as cardiac, gastric, nerve, and drug delivery, for example. Portions of the subject matter disclosed may be combined in embodiments not explicitly set forth while remaining within the spirit and scope of the disclosure. Further, the disclosure is not limited to systems with two devices, or, for that matter, to communication between an implantable and external medical device. Thus, other embodiments may include communication between implantable devices, or external devices.

Other embodiments of the present disclosure will become readily apparent to those skilled in the art from this disclosure. As will be realized, the disclosure is capable of other and different embodiments and its several details are capable of modifications in various respects that may be realized by one having ordinary skill in the art reading this disclosure, all without departing from the spirit and the scope of the present disclosure. Accordingly, the drawings and detailed description are to be regarded as illustrative in nature and not as restrictive.

What is claimed is:

1. A method for adjusting a timeout period of a communication session, comprising:
   establishing a communication session between an implantable medical device and at least one other device, wherein a session key is transmitted between the implantable medical device and the at least one other device in establishing the communication session, the session key allowing one or both of programming of the implantable medical device by the at least one other device and decryption of information transmitted between the implantable medical device and the at least one other device during the communication session;
   setting a time period interval of the session key;
   receiving a communication session close trigger event after an amount of time greater than zero has passed from the establishment of the communication session and while the communication session is ongoing;
   performing a count of the time period interval in response to the reception of the communication session close trigger event; and
   disabling the session key in response to expiration of the time period count, wherein establishing, setting, receiving, performing, and disabling are each performed at least in part by one or both of the implantable medical device and the at least one other device.

2. The method of claim 1, wherein the time period interval is set before the session key is transmitted between the implantable medical device and the at least one other device in establishing the communication session.

3. The method of claim 1, further comprising evaluating a time duration for each of a plurality of previous communication sessions involving at least one of the implantable medical device and the at least one other device, wherein the time period interval of the session key is set based on the evaluation of the time duration for each of the plurality of previous communication sessions.

4. The method of claim 1, wherein setting the duration of the time period comprises evaluating at least one predefined criteria to determine the time period.

5. The method of claim 4, wherein the predefined criteria includes a category of a clinical procedure indicated to be performed as part of the communication session.

6. The method of claim 1, wherein setting the duration of the time period comprises receiving a predetermined time period input from the at least one other device, the at least one other device being a programmer configured to communicate with the implantable medical device.

7. The method of claim 1, wherein establishing the communication session comprises generating the session key, wherein the session key is generated by the at least one other device and is ephemeral.

8. The method of claim 1, wherein disabling the session key comprises deleting the session key from the device to which it was transmitted.

9. The method of claim 1, further comprising:
   receiving an indication of activity during the time period count; and
   resetting the time period count responsive to receiving the indication of activity.

10. The method of claim 1, wherein the trigger event comprises one of an inactivity interval, a session link loss indication, a close service request, expiration of a predefined interval, and a communication session interruption.

11. The method of claim 1, wherein the time period count is performed by the device of the plurality of devices to which the session key was transmitted.

12. The method of claim 1, further comprising generating an alert to a user based on the count of the time period interval.

13. A system for adjusting a timeout period of a communication session in transcutaneous communications, comprising:
   an implantable medical device having communication circuitry;
   an external device having communication circuitry, the communication circuitry of the implantable medical device and the communication circuitry of the external device configured to establish a communication session between the implantable medical device and the external device and to transmit a session key between the communication circuitry of the implantable medical device and the communication circuitry of the external device in establishing the communication session, the session key allowing one or both of programming of the implantable medical device by the external device and decryption of information transmitted between the implantable medical device and the external device during the communication session; and
   control circuitry configured to set a time period interval of the session key, receive a communication session close trigger event after an amount of time greater than zero has passed from the establishment of the communication session and while the communication session is ongoing, perform a count of the time period interval in response to the reception of the communication session close trigger event, and disable the session key in response to expiration of the time period count.

14. The system of claim 13, wherein the control circuitry is further configured to evaluate a time duration for each of a plurality of previous communication sessions involving at least one of the implanted medical device and the external device, wherein the time period interval of the session key is set based on the evaluation of the time duration for each of the plurality of previous communication sessions.

15. The system of claim 13, wherein the control circuitry is configured to evaluate at least one criterion and set the duration of the time period based on the evaluation of the at least one criterion.

16. The system of claim 15, wherein the control circuitry is configured to receive an indication that establishment of the communication session is desired by a user, wherein the evaluation of the at least one criteria determines a category of a clinical procedure and the control circuitry sets the duration of the time period based on the category for the communication session.

17. The system of claim 13, wherein the control circuitry is distributed between the implantable medical device and the external device.

18. The system of claim 13, wherein the control circuitry is located entirely within a housing of the implantable medical device.

19. The system of claim 13, wherein the control circuitry is located entirely within a housing of the external device.

20. The system of claim 13, wherein the control circuitry is further configured to generate the session key as part of establishing the communication session and the session key is ephemeral.

21. The system of claim 13, wherein the control circuitry is configured to disable the session key by invalidating the session key for allowing one or both of programming of the implantable medical device by the external device and decryption of information transmitted between the implantable medical device and the external device during the communication session.

22. The system of claim 13, wherein the control circuitry is configured to receive an indication of communication activity during the time period count and reset the time period count responsive to receiving the indication of communication activity.

23. The system of claim 13, wherein the control circuitry is configured to generate an alert to a user based on the count of the time period interval.

24. A system for adjusting a timeout period of a communication session, comprising:
- means for establishing a communication session between an implanted medical device and at least one other device, wherein a session key is transmitted between the implanted medical device and the at least one other device in establishing the communication session, the session key allowing one or both of programming of the implanted medical device by the at least one other device and decryption of information transmitted between the implanted medical device and the at least one other device during the communication session;
- means for setting a time period interval of the session key;
- means for receiving a communication session close trigger event after an amount of time greater than zero has passed from the establishment of the communication session and while the communication session is ongoing;
- means for performing a count of the time period interval in response to the reception of the communication session close trigger event; and
- means for disabling the session key in response to expiration of the time period count.

25. A computer readable medium comprising instructions for causing a medical device to adjust a timeout period of a communication session by performing steps comprising:
- establishing a communication session between an implantable medical device and at least one other device, wherein a session key is transmitted between the implantable medical device and the at least one other device in establishing the communication session, the session key allowing one or both of programming of the implantable medical device by the at least one other device and decryption of information transmitted between the implantable medical device and the at least one other device during the communication session;
- setting a time period interval of the session key;
- receiving a communication session close trigger event after an amount of time greater than zero has passed from the establishment of the communication session and while the communication session is ongoing;
- performing a count of the time period interval in response to the reception of the communication session close trigger event; and
- disabling the session key in response to expiration of the time period count.

* * * * *